(12) United States Patent
Messinger et al.

(10) Patent No.: US 6,197,198 B1
(45) Date of Patent: Mar. 6, 2001

(54) METHOD AND DEVICE FOR PARALLEL CHROMATOGRAPHY

(75) Inventors: Josef Messinger, Sehnde; Frank Gundlach; Ernst Sinner, both of Hannover, all of (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 09/367,056

(22) PCT Filed: Feb. 2, 1998

(86) PCT No.: PCT/EP98/00535

§ 371 Date: Oct. 28, 1999

§ 102(e) Date: Oct. 28, 1999

(87) PCT Pub. No.: WO98/35227

PCT Pub. Date: Aug. 13, 1998

(30) Foreign Application Priority Data

Feb. 6, 1997 (DE) ............................................. 197 04 477

(51) Int. Cl.$^7$ .................................................. B01D 15/08
(52) U.S. Cl. ........................... 210/656; 210/198.2; 95/82; 96/101; 422/70
(58) Field of Search ...................... 210/635, 656, 210/659, 198.2, 232, 238; 95/82; 96/101; 422/70; 436/161

(56) References Cited

U.S. PATENT DOCUMENTS

| | | | |
|---|---|---|---|
| 4,766,082 | * 8/1988 | D'Autry | 210/198.2 |
| 5,395,521 | * 3/1995 | Jagadeeswaran | 210/656 |
| 5,443,734 | * 8/1995 | Fetner | 210/656 |
| 5,585,070 | * 12/1996 | Lessard | 210/198.2 |
| 5,811,665 | * 9/1998 | Gregor | 210/656 |
| 5,872,010 | * 2/1999 | Karger | 210/198.2 |
| 5,906,724 | * 5/1999 | Sammons | 210/198.2 |
| 6,019,897 | * 2/2000 | Horsman | 210/656 |
| 6,090,278 | * 7/2000 | Lally | 210/656 |

FOREIGN PATENT DOCUMENTS

| | | | |
|---|---|---|---|
| 1 966 363 | * 9/1972 | (DE) | 210/198.2 |
| 25 45 997 | * 4/1977 | (DE) | 210/198.2 |
| 39 27 863 | * 2/1991 | (DE) | 210/198.2 |
| 425 297 | * 5/1991 | (EP) | 210/198.2 |
| 75 11764 | * 11/1975 | (FR) | 210/198.2 |
| 1095569 | * 12/1967 | (GB) | 210/198.2 |

* cited by examiner

*Primary Examiner*—Ernest G. Therkorn
(74) *Attorney, Agent, or Firm*—Evenson, McKeown, Edwards & Lenahan, P.L.L.C.

(57) ABSTRACT

The invention relates to a device or equipment as well as to a method for the simultaneous, fractionating operation of a plurality of parallel chromatographic columns. It is particularly advantageous to apply this equipment and method in research, in the framework of organic synthesis for simultaneous, parallel separation, isolation and purification of a plurality of chemical compounds, e.g. of potential new active ingredients for medicaments, particularly also on the semi-preparative scale.

16 Claims, 3 Drawing Sheets

METHOD AND DEVICE FOR PARALLEL CHROMATOGRAPHY

REFERENCE TO RELATED APPLICATIONS

This application is a 371 of PCT/EP98/00535 filed Feb. 2, 1998.

BACKGROUND OF THE INVENTION

The invention relates to a device or equipment as well as to a method for the simultaneous, fractionating operation of several parallel chromatography columns. The equipment and the method can be utilized in a particularly advantageous manner in research, within the context of organic synthesis for simultaneous, parallel separation, isolation, and purification of many chemical compounds, such as new active ingredients for medicaments, and especially on the semi-preparative scale.

Column chromatography is a typical method for separating substance mixtures in organic synthesis, especially in the form of a liquid-solid chromatography. Modern pharmaceutical research, therefore, would be unthinkable without column chromatography as a method for isolating and subsequently identifying synthesized organic substances. Since the identification a new type of active ingredient continues to be a difficult and expensive enterprise which necessitates the synthesis of a large number of chemical compounds, the need for innovations with respect to equipment and method still persists. The role of so-called combinatorial synthesis is becoming increasingly important for both the search for as well as the optimization of guide structures, in order to produce chemical compounds within smaller and smaller periods of time. To the extent that systematic molecular variation by way of combinatorial synthesis results in a plurality of different compounds extremely quickly, other methods applied within the context of searching for active ingredients—for example methods for separating substance mixtures or for isolating and purifying individual substances—must also stay apace with the heightened synthesis capacity. For example, although it still was sufficient for classical synthesis procedures to subject the synthesized compounds to a chromatography individually and, if necessary, sequentially, modern synthesis methods with a higher capacity as well as combinatorial chemistry also require a heightened output capacity during the separation of substance mixtures or during the isolation and purification of synthesized compounds, and especially on a semi-preparative scale.

SUMMARY OF THE INVENTION

The object thus was to provide a simple and efficient device for the simultaneous parallel execution of column chromatographies, especially for the semi-preparative scale.

The object is achieved by means of the device or equipment which are stated in the claims as well as by means of the method for column chromatography described.

Accordingly, the invention particularly concerns a device for the simultaneous parallel execution of a particular number n of column chromatographies, in which the device is characterized by a) a mounting base, preferably in the form of a base trough which serves to accommodate one or several removable test tube racks (fraction collectors), wherein these test tube racks are adapted in their measurements, either individually or collectively, to the internal dimensions of the mounting base, preferably the base trough, such that an arrangement of m rows lying at a distance from one another with n test tubes standing at a distance in juxtaposition can be effected, wherein the mounting base, preferably the base trough, optionally can have an additional solvent drain arranged on one or both of the ends (in "position 0" and/or "end-position");

b) a slide rail which is arranged parallel to each longitudinal side of the mounting base, preferably a base trough, with a controllable, motor-driven carriage;

c) a movable bridge which is arranged on the carriage—by means of which said bridge can be moved across the mounting base at a distance—, and which serves as a support for the fixed or, optionally, interchangeable accommodation of a plurality of chromatographic columns ("column support bridge");

d) a number n of chromatographic columns which are arranged in rows on the column support bridge parallel to the end of the mounting base, preferably a base trough, in such a way that the positions of the dropper tips of the line of chromatographic columns to be traversed is aligned with the positions of the test tubes in the individual rows, in the process of which the chromatographic columns can be designed for working under pressure;

e) a solvent container for accommodating an eluting agent or, optionally, several solvent containers for accommodating various eluting agents, in which the solvent container or containers also optionally can be designed as pressure containers and in which the solvent container or containers also can be arranged to be mounted on the column support bridge above the chromatographic columns;

f) fixed or flexible supply tubes for introducing the eluting agent or agents from the solvent container or containers into the chromatography columns;

g) a motor drive for moving the carriage with the column support bridge on the slide rails and an electronic control device for automatic control, in particular of the time interval, the rate of feed, and the position of the column support bridge along the mounting base, preferably along the base trough;

in which the number n refers to the chromatographic columns arranged on the column support bridge and represents a number larger than 5;

and in which the number m refers to the possible test tube rows which can be traversed by the column support bridge.

The particular dimensions of the device or the individual components, as well as the exact arrangement of the components can be embodied in accordance with the needs and desires of the respective user. In this way, the structural design and production of the inventive device can be accomplished without particular difficulty. Aside from the components described above, more components which are tailored to further user requirements or to other requirements (such as safety regulations) can be provided, if desired. For example, the mounting base, designed as a base trough, can be fitted with a suctioning device for suctioning the solvent vapors from the mounting base or trough area and its surroundings. Moreover, if desired, the entire device can also be equipped with a shrouding cover or an object suctioner, to the extent that the dimensioning of the device makes it impossible to work in conventional laboratory hoods. The mounting base itself comprises two parallel longitudinal walls as well as two perpendicular lateral walls (ends, or a top and a bottom), as well as a floor plate connected tightly to the lateral walls to form a base trough. The mounting base or trough is securely connected to the slide rails which are arranged parallel to the longitudinal walls of the mounting base or trough. In this way, the carriage moving inside can be moved precisely to a particular position along the mounting base or trough. The test tube racks (fraction collectors) which can be placed into the mounting base or trough are designed in the usual manner and are suited for accommodating test tubes with various diameters which are commercially available. If desired, the test tube rack can be fitted with a suitable cover which serves as a funnel and as a splash guard. Furthermore, a test tube rack which prevents the transposition of test tubes is advantageous because the subsequent processing of the samples can be facilitated. The chromatographic columns are likewise columns having the desired dimensions which comprise standard commercial sizes, such as glass tubes with a thread which can be sealed at the top by means of threaded caps or in some other suitable manner so as to be pressure-tight. The actuator for moving the carriage on the slide rails and the electronic control device are constructed in a conventional manner or in the manner typical for the market. The electronic control device serves to regulate automatically the time interval, the rate of feed, and the position of the column support bridge above the test tubes as well as to shut down the device automatically after the predetermined fraction count has been attained (corresponds to the number of test tube rows) or after the end position has been reached. A solvent drain as a device for drop collection can be advantageous in the end position (that is at the bottom of the plate or trough).

Conventional solvent containers can be used to introduce the eluting agent or agents into the chromatographic columns. While the column chromatography is being carried out, the eluting agents can be pumped via the supply lines to the ends of the chromatographic columns under normal pressure by means of one or several pumps, e.g. hose pumps.

Generally, it is advisable to operate more than 5 columns simultaneously, in order to fully utilize the advantages of the inventive device for parallel chromatography. For this reason, generally speaking, a number of chromatographic columns from N=6 to 15, preferably a number from N=6 to 10, can be arranged on the column support bridge. If necessary, more chromatographic columns also can be mounted next to one another on the column support bridge, whereby this is not advisable due to the increased construction expense associated with it.

In another variation of the invention, it is contemplated to carry out the parallel column chromatography under elevated pressure. The inventive device distinguishes itself here in that the components of the device—especially the chromatographic columns, the solvent container or containers, the supply lines, the connecting elements, and the sealing elements—have been structurally designed for working under pressure, preferably for working under elevated pressures of up to 10 bar, as necessary.

In another, advantageous variation of the invention, it is contemplated to arrange the solvent container or containers of the inventive device such that the solvent container or containers is or are firmly attached to the column support bridge above the chromatographic columns.

The solvent container can hereby be constructed with sub-divisions in the interior for the application of various eluting agents, or even without sub-divisions, to the degree that the parallel chromatographies are to be executed predominantly with only one homogenous eluting agent.

Furthermore, it is also possible to arrange several separate solvent containers next to one another above the chromatographic columns on the column support bridge. In any event, it is advisable to design the solvent container or containers in this variation of the invention for working under elevated pressure. The solvent container or containers therefore generally consist of a pressure-tight metal hollow chamber which either can be fashioned itself to be resistant to the solvent or which can be fitted with a solvent-resistant coating. Moreover, the solvent container or containers have a feed opening for the solvent which can be sealed in a pressure-resistant manner as well as an inlet for the pressure gas (for example nitrogen or a noble gas) which is desirably connected to a manometer for measuring and regulating the pressure. For safety-related reasons, the closure of the inlet opening can be designed as a rupture disk and can have a pressure-relieving action. In order to drain the solvent, the solvent container or containers generally have another suitable escape valve at the bottom.

The invention also concerns a method for the simultaneous parallel execution of a particular number n of fractionating column chromatographies by means of the inventive device. The device according to the invention distinguishes itself in that n chromatographic columns are fed and conditioned in the conventional manner with solid phase and solvent to begin with; thereafter, the samples are introduced into the ends of the columns, and optionally, the column tops are sealed. After this, the actual fractionating column chromatographies are initiated by beginning to introduce the solvent into the ends of the chromatographic columns with the chromatographic columns in position over the first row of test tubes (that is, in position 1 or the starting position), after which the individual test tube rows are moved into the predetermined positions and time intervals while adhering to a pre-determined holding time over each test tube, optionally under elevated pressure, in accordance with the program of the electronic control device, beginning with row 1 through to row m, and the individual fractions are collected in the test tubes. If desired, filling and conditioning the chromatographic columns as well as the introduction of samples can be performed above a solvent drain which is arranged parallel to the column end (in "position 0") before the parallel chromatographic columns are moved into position over the first test tube row (in "position 1" or the "starting position") to begin the parallel fractionating column chromatography.

If a glass test tube rack is used with the covering plate described above, the column support bridge can be moved in continuous motion over the test tubes at an appropriate rate. The distribution of the fractions among the individual test tubes then ensues by means of the respective, funnel-shaped constructions on the covering plate above the individual test tubes; the holding time which is stated above within the scope of the inventive method then hereby corresponds to the time interval which is required for traversing a funnel cone.

The inventive device as well as the inventive method have a number of advantages compared to conventional devices and methods for column chromatography. For example, the invention enables the simultaneous operation of a certain number of parallel chromatographic columns in an automated operating sequence. While the conventional operation of individual columns in juxtaposition or sequentially requires a larger amount of equipment (for example several fraction collectors, pumps, etc.) and also means higher expense with respect to time, operation, and sampling for the laboratory personnel when preparing for and performing the individual chromatographies, the inventive method with the inventive device, in contrast, can be carried out in an efficient, automated operational sequence while significantly decreasing operating time. Within the framework of the automated operational sequence with the inventive method, the individual steps of a column chromatography can be efficiently executed in a parallel manner. First, all the columns of the parallel chromatography are filled and conditioned with solid phase and solvent. In the next operational step, all the columns of the parallel chromatography are loaded with the samples. In addition, especially with the variation with only one solvent container connected to the column support bridge, the introduction of eluting agents and also the generation and regulation of pressure works very efficiently for the laboratory personnel. Moreover, the device which is proposed in accordance with the invention and the method for parallel chromatography facilitate a heightened output capacity in comparison to conventionally-operated column chromatographies.

Further structural embodiments and advantages of the invention can be found in FIGS. 1 through 3, by means of which examples the invention is further illustrated without limiting its scope.

DESCRIPTION OF THE PREFERRED EMBODIMENTS

Figure 1:
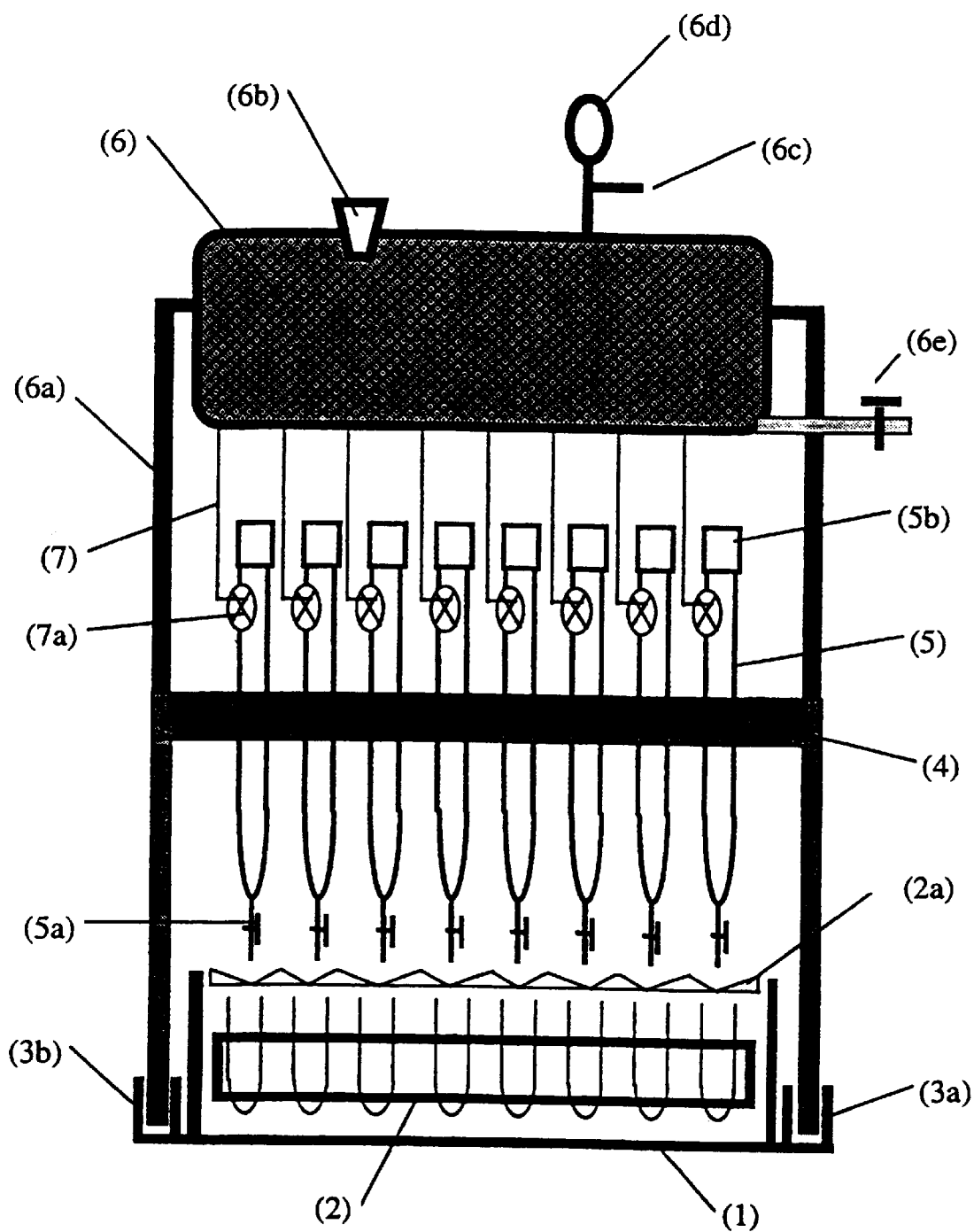
FIG. 1 shows a schematic depiction of a parallel chromatography system.

FIG. 1:

A schematic depiction of an inventive parallel column chromatography system (cross-sectional perspective, seen from the top or bottom; a pressure-tight solvent container, connected to the column support bridge; parallel operation of 8 chromatographic columns. The reference numbers in FIG. 1 hereby refer to the following:

(1)=base trough (2)=test tube rack with m rows, with 8 test tubes in each row (2a)=plate (covering) as a splash guard and a feed device (funnel)

(3a), (3b)=side rails on the longitudinal side walls of the base trough (4)=column support bridge for either the fixed or interchangeable accommodation of chromatographic columns; in this case, 8 chromatographic columns (5)=chromatographic columns (5a)=dropper tips of the chromatographic columns with or without a valve (such as tapered plugs or solenoid valves)

(5b)=column closure; for example, a threaded cap with or without a seal (6)=solvent container; in this case, a one-piece form designed to withstand pressure (6a)=support for the solvent container arrangement and for the connection to the column support bridge (6b)=solvent inlet with a rupture disk and a pressure-release valve which can be sealed (6c)=inlet for pressure gas (for example nitrogen or a noble gas), associated here with a manometer (6d) for measuring pressure and, optionally, a valve for pressure regulation or an escape valve (6d)=manometer (6e)=emergency drain valve for solvent (7)=solvent supply lines for supplying the eluting agent from the solvent containers to the tops of the columns, with a supply valve (7a); the supply valves (7a) can be embodied as tapered plugs (for example as a two-way or three-way valve) or as solenoid valves.

Figure 2:
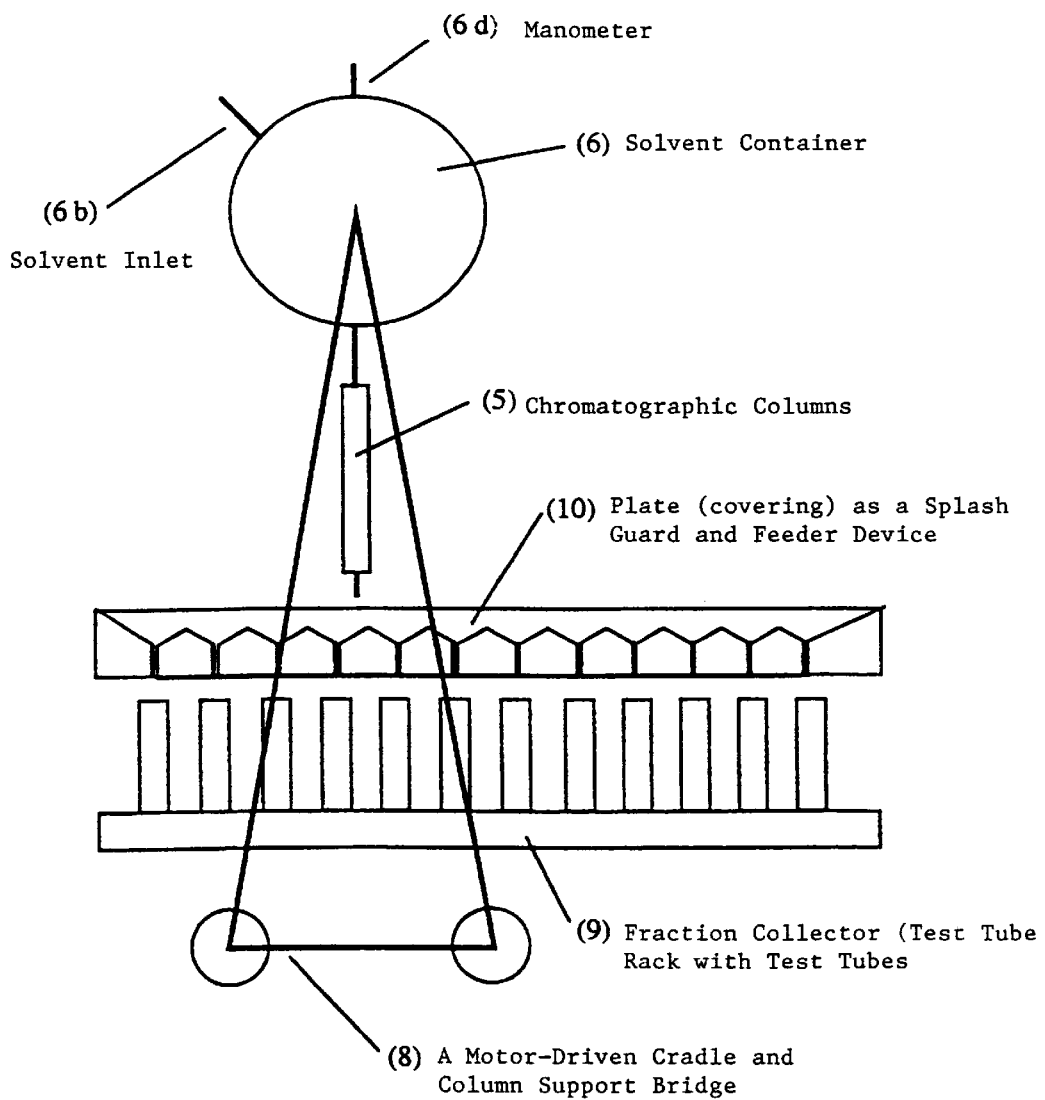
FIG. 2 shows a parallel chromatography system viewed schematically in longitudinal view.

FIG. 2:

A parallel chromatography system viewed schematically in longitudinal view. The components and reference numbers given in FIG. 2 correspond to the following, to the extent that they have not been indicated in FIG. 1 already:

(8)=a motor-driven carriage and column support bridge (9)=fraction collector=test tube rack wit test tubes=(2)

(10)=plate (covering) as a splash guard and feed device=(2a)

Figure 3:
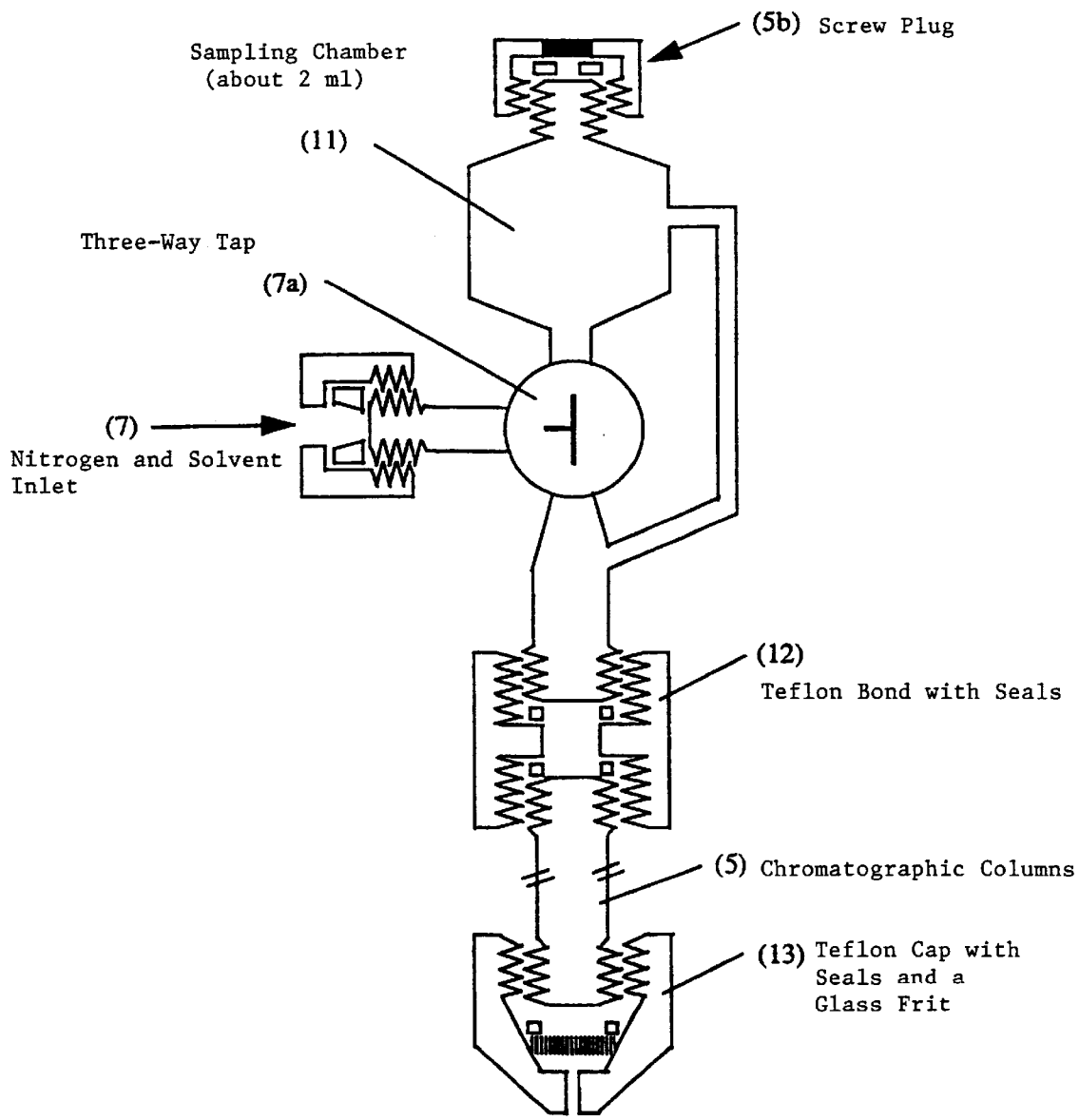
FIG. 3 shows columns for a parallel chromatography system, viewed schematically.

FIG. 3:

Columns for a parallel chromatography system, viewed schematically. The components and reference numbers given in FIG. 3 refer to the following here:

(5b)=threaded cap (7)=nitrogen and solvent inlet (7a)=three-way valve (11)=sample chamber, in this example about 2 ml (12)=Teflon joint with seals for joining column and cap (13)=Teflon closure with seals and a glass frit as a column drain (instead of 5a)

What is claimed is:

1. An apparatus for simultaneously carrying out a number n of fractionating column chromatographies, said apparatus comprising:

a) a mounting base containing one or more removable test tube racks such that an array of m spaced rows of n test tubes in each row is formed;

b) a pair of parallel side rails extending respectively along longitudinal sides of said mounting base and a controllable, motor-driven carriage movable along said side rails;

c) a column support bridge mounted on said carriage so as to be movable therewith over the m rows of test tubes in said array of test tubes in said mounting base;

d) a number n of chromatographic columns mounted on said bridge in a row parallel to the rows of test tubes in said array; said n chromatographic columns each having at the bottom thereof a dropper tip which is positioned such that as the carriage and bridge move over the array of test tubes in the mounting base, the line of movement of the dropper tip is aligned with a respective test tube in each row of test tubes;

e) at least one solvent container mounted on said carriage for accommodating an eluting agent;

f) a plurality of supply lines connected between said at least one solvent container and said chromatographic columns for introducing solvent from said at least one container into said columns; and g) a motor drive for moving the carriage and column support bridge along said side rails over the mounting base and an electronic control device for automatically controlling the movement of said carriage and column support bridge; and wherein n represents a whole number greater than 5.

2. An apparatus according to claim 1 wherein said mounting base is in the form of a trough.

3. An apparatus according to claim 1 wherein said mounting base is provided with at least one solvent drain at one or both ends.

4. An apparatus according to claim 1 wherein said plurality of chromatographic columns are fixedly mounted on said bridge.

5. An apparatus according to claim 1 wherein said plurality of chromatographic columns are detachably mounted on said bridge so as to be interchangeable.

6. An apparatus according to claim 1 wherein said chromatographic columns are pressure-tight and operate under elevated pressure.

7. An apparatus according to claim 1 comprising a plurality of solvent containers for different solvents mounted on said carriage.

8. An apparatus according to claim 1 wherein said at least one solvent container is pressure-tight and operates under elevated pressure.

9. An apparatus according to claim 8 wherein the at least one solvent container, the plurality of supply lines and the chromatographic columns operate under an elevated pressure of up to 10 bar.

10. An apparatus according to claim 1 wherein said at least one solvent container is mounted on said bridge above the chromatographic columns.

11. An apparatus according to claim 1 wherein said supply lines are flexible pressure tubes.

12. An apparatus according to claim 1 wherein said electronic control device controls both the speed and the position of the carriage and column support bridge.

13. An apparatus according to claim 1 wherein n is a whole number from 6 to 15.

14. An apparatus according to claim 13 wherein n is a whole number from 6 to 10.

15. A method for simultaneously carrying out a number n of parallel fractionating column chromatographies, said method comprising the steps of:

providing an array of m rows of n test tubes in each row and a number n of chromatographic columns supported in a row on a bridge mounted on a carriage so as to be movable over the array of test tubes;

charging and conditioning the chromatographic columns with solid phase and solvent in a start position above a solvent drain;

loading a sample at the top of each chromatographic column;

introducing an eluting agent from at least one solvent container mounted on said bridge into the tops of the chromatographic columns to initiate chromatography of the samples;

moving the row of chromatographic columns over successive rows of test tubes in said array under the control of an electronic controller so that each chromatographic column is positioned for a predetermined time interval over a respective test tube of each of the m rows of test tubes; and collecting individual chromatography fractions from the chromatography columns in the respective test tubes of successive rows.

16. A method according to claim 15 wherein the chromatographies are carried out under an elevated pressure of up to 10 bar.

* * * * *